(12) United States Patent
Koikkalainen et al.

(10) Patent No.: US 7,840,510 B2
(45) Date of Patent: Nov. 23, 2010

(54) METHOD FOR INFERRING THE STATE OF A SYSTEM

(75) Inventors: Juha Koikkalainen, Tampere (FI); Jyrki Lötjönen, Tampere (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 703 days.

(21) Appl. No.: 11/798,583

(22) Filed: May 15, 2007

(65) Prior Publication Data

US 2007/0271209 A1     Nov. 22, 2007

(51) Int. Cl.
*G06F 17/00*     (2006.01)
*G06N 5/00*     (2006.01)
(52) U.S. Cl. .............................. 706/45; 704/2; 702/182
(58) Field of Classification Search ........................ None
See application file for complete search history.

(56) References Cited

U.S. PATENT DOCUMENTS 5,377,308 A * 12/1994 Inoue et al. .................... 706/52

2006/0172436 A1 * 8/2006 Hattori et al. ............... 436/518

OTHER PUBLICATIONS

Juha Koikkalainen et al; Estimation of Disease State Using Statistical Information from Medical Imaging Data; Oct. 6, 2006; MICCAI 2006, Copenhagen, Denmark; MICCAI 2006 Workshop proceedings.
QSMBI (Quantitative Shape Modelling of Biomedical Images) Workshop, Tentative Schedule, Copenhagen, Denmark, May 17, 2006, pp. 1-2.
Jyrki Lotjonen et al , "From cardiac image analysis towards personalized healthcare," MICCAI 2006 Workshop, Copenhagen, Denmark, Oct. 6, 2006, pp. 1-11.
Juha Koikkalainen et al., "Estimation of Disease State Using Statistical Information from Medical Imaging Data", QSMBI Workshop, Copenhagen, Denmark, May 17, 2006, pp. 1-9.

* cited by examiner

*Primary Examiner*—Donald Sparks
*Assistant Examiner*—Kalpana Bharadwaj
(74) *Attorney, Agent, or Firm*—Venable LLP; Eric J. Franklin

(57) ABSTRACT

An apparatus, and a method, comprising: computing a measure of goodness for each of at least two dimensions of a system linked to a first state of the system and a second state of the system; computing a weighting for each of at least two dimensions linked to a studied system, the weightings describing the differences of said at least two dimensions in relation to said first state and said second state; and inferring the state of the studied system based on said measures of goodness and said weightings.

22 Claims, 9 Drawing Sheets

| Disease: | Modality: | Population: | | |
|---|---|---|---|---|
| ☐ CAD<br>☐ DCM<br>☐ ICM<br>☐ HCM<br>☐ D5<br>☐ D6 | ☐ MRI<br>☐ CT<br>☐ PET<br>☐ ECHO<br>☐ SPECT<br>☐ RA | ☐ Sex<br>○ Male<br>○ Female<br>☐ Age<br>○ <50 y<br>○ >50 y | | ☐ Weight<br>○ <80 kg<br>○ >80 kg<br>☐ Smoking<br>○ y<br>○ n |

| Measure: | | | Structure: | |
|---|---|---|---|---|
| ☐ EF<br>☐ EDV<br>☐ ESV | ☐ SV<br>☐ $WT_{ED}$<br>☐ $WT_{ES}$ | ☐ $WT_{ED\text{-}ES}$<br>☐ SM<br>☐ MF | ☐ LV<br>☐ RV<br>☐ MYO | ☐ LA<br>☐ RA |

Fig. 1

METHOD FOR INFERRING THE STATE OF A SYSTEM

FIELD OF THE INVENTION

The invention relates to the process of inferring the state of a system and classifying data. The invention relates to the apparatus for inferring the state of a system and visualizing the state. The invention relates to the computer program product for inferring the state of a system and visualizing the state.

BACKGROUND OF THE INVENTION

Any arbitrary system can have at least two states. The system can be, for example, an apparatus, a human body, or a financial entity. Typically, the system either functions correctly (normal state) or has a malfunction (error state). There may be several normal and/or error states. A good example is the healthiness of a human: he or she can be healthy (normal state) or have a disease (error state), in which case the number of the error states is very large. The state of the system defines in which normal or error state the system is and how much the state of the system differs from a reference state specified beforehand. For example, in medical applications the state of the system defines the disease a patient has and how far the disease has advanced, as compared with the normal, healthy state, or the state of the system defines the malfunction of an apparatus and how severe the malfunction is.

Computerized methods are needed in the above-mentioned analyses of the state of the system to efficiently utilize multidimensional data and to find complex correlations in the data. Each dimension relates to an aspect of the particular system that is being measured and from which measurement values are gathered. Typically, the computerized methods give only a classification as an output. However, in many applications the computerized methods cannot make the final decision because of possible erroneous decisions, but a human user has to make the final decision. The computerized methods should be regarded as an extra resource for users, which supports the decision making but does not try to replace the users and their knowledge and experience.

The computerized methods should provide the user with an accurate, reliable, continuous index on the state of the system, not just a binary classification result (normal or failure). For example, in computer-assisted diagnosis, the computerized method has to give to a physician information on how probable it is that a patient has a disease, so that this information would be helpful for the physician in the decision-making.

In the conventional computerized methods, the classification is carried out based on only one measurement and the detection is carried out using one error state and one normal state only. One measurement may give decent classification results when there is only one possible error state. However, in practice, the possible error state is not known, but the data of the system has to be compared with all existing error states. However, measurement values are probably overlapping when many error states are studied simultaneously, and the classification is inaccurate when only one measurement is used. On the other hand, if the possible error state of the system is detected, it would be useful to know how severe the error state is.

SUMMARY OF THE INVENTION

If many measurements are used to define the state of the system, regression analysis is one possible technique. However, in the regression analysis, it is assumed that the state of the system is known in a training set, i.e. the values of the dependent variable of the regression analysis have to be known. This is not the case in many applications, because the severity of the state is unknown. The invention enables the analysis of the state of a system from multiple measurements even when it is not known how much the state of the system differs from the reference state of the training set. In addition, visualization tools for the analysis and comparison of the system and group data are presented.

The invention infers the state of a system by studying a set of measurements measured from the system and databases of at least some possible states of the system. The set contains measurements relating to at least two dimensions of the system.

An object of the invention is to provide a method to infer the state of a system from a set of measurements measured from the system.

Another object of the invention is to provide a method for classifying data.

The invention infers a state of the system by studying a set of measurements measured from the system and the databases of at least some possible states. A subgroup, if needed, can be selected from each database so that the subgroup represents as accurately as possible the particular state. Then, an index that describes the state of the system of interest is determined using a method based on statistical analysis and distance or probabilistic measures.

The index obtained as a result indicates the state of the system: the larger the index is the more probable it is that the system is in the particular state and the more distinct the state is.

Another object of the invention is to provide visualization tools to visualize the state of the system for fast and easy detection of similarities and differences between the system and the states of interest. In addition, the visualization tools may be used to compare the characteristics of two or more states.

A visualization tool based on a tree structure may be used to visualize the state of the system, when compared with a reference state, using e.g. colour codes, arrows, pointers or indicators.

Another visualization tool can be used to simultaneously visualize the measurement values of the system when compared with the reference state as well as the differences between the reference state and the state of interest.

Additionally, other suitable visualization tools can be used to visualize the state of the system, e.g. different sizes of the boxes presented in figures and representing the measurement values of the system or the reference and study states.

BRIEF DESCRIPTION OF THE DRAWINGS

FIG. 1 illustrates an example of the selection of the features in the visualization tool.

DETAILED DESCRIPTION OF THE INVENTION

The invention infers the state of a system from a set of measurements determined from the system of interest. An index is defined for the studied system, which describes how probable it is that the system is in a particular state and how distinct the state is.

Figure 6:
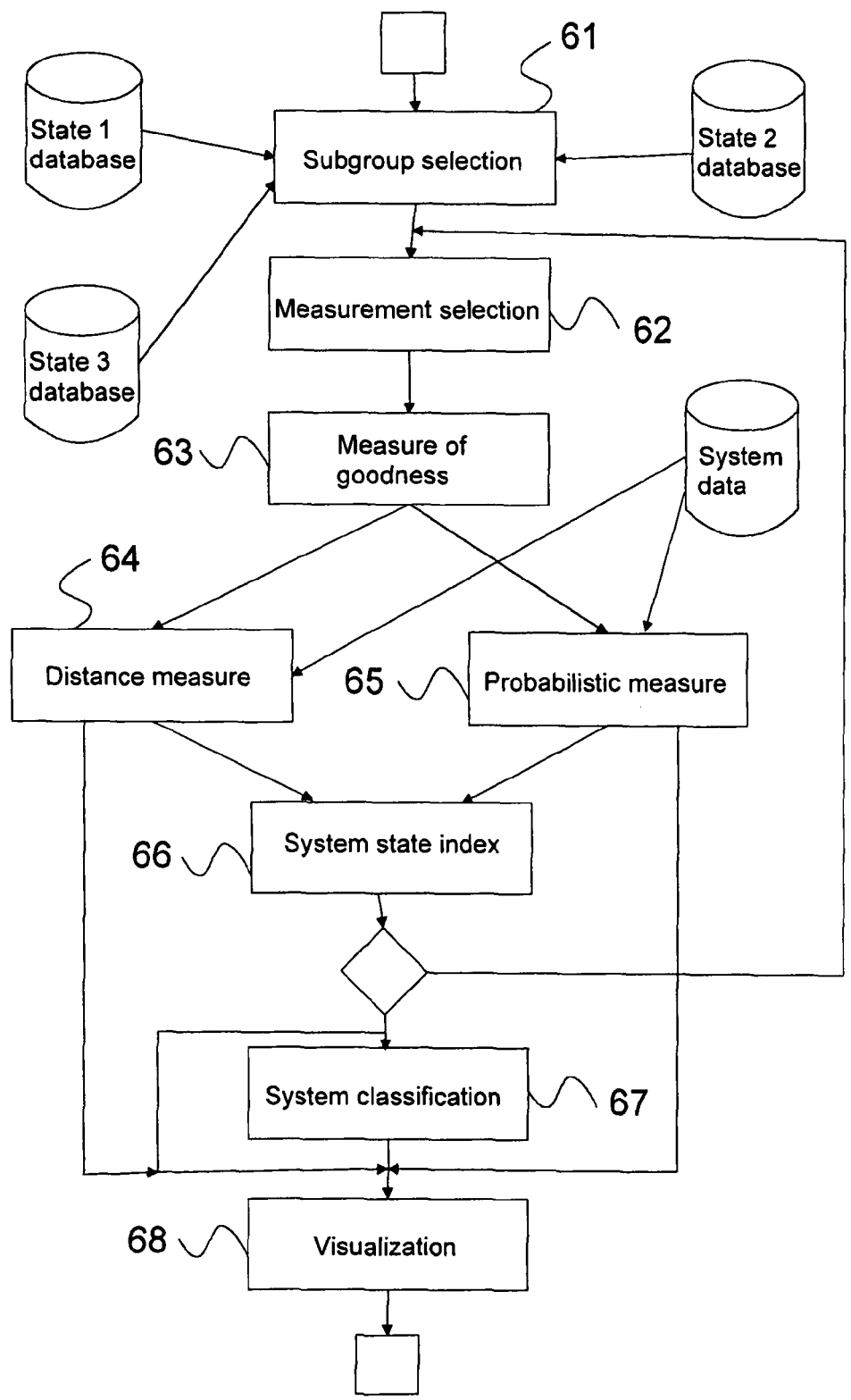
FIG. 6 illustrates embodiments of the invention.

The analysis is carried out by comparing the system data with the data in the databases of a reference state and a study state using statistical methods. The system data contains the measurement values that describe the state of the system. The database of a state includes data from at least one example of a system that is in a particular state. One state, either a real or a synthetic state, is selected as the reference state. For example, if the studied system is a human heart and the reference state is the healthy state, the database of the reference state contains measurement values from at least one healthy heart describing, for example, the anatomy and function of the heart. The study state can be a heart disease, and the database of the study state contains measurement values from at least one heart with the heart disease. FIG. 6 shows embodiments of the invention. Method steps relating to FIG. 6 are presented in the disclosure below describing the embodiments.

A representative subgroup of examples from a database

First, the characteristics of the reference and study states have to be established from corresponding databases (e.g. the state 1 database and the state 2 database in FIG. 6). However, in the study state database, there may be many examples, i.e. several sets of measurements, that are very close to the reference state, and therefore do not give information on the study state. There may also be outliers in the reference state database that disturb the analysis. The objective is to generate such subgroups of examples from the databases (step 61) which represent as accurately as possible the characteristics of the reference and study states.

There are several ways to generate a subgroup from a database.

1) All the examples in the database are used.

2) For the study state, the examples that differ most from the reference state are searched. This can be done using Cartesian distance, Mahalanobis distance, or statistical tests. The number of the selected examples can be defined using a constant number, or a threshold for the distances or the results of the statistical tests. For the reference state, the outliers are detected and removed from the database.

3) One synthetic example is generated that represents the worst case of the study state. For each measurement, the N extreme measurement values are searched. The largest values are searched if the measurement values of the study state are larger than the values of the reference state, and respectively the smallest values are searched if the measurement values in the study state are smaller than in the reference state. Then, the mean or median of the N extreme measurement values is computed for each measurement.

4) The subgroups of the reference and study states are created using other information, for example, demographic data.

An Index for the State of the System

By utilizing the generated subgroups, an index is generated that describes the state of the studied system. This can be done using either distance measures or probabilistic measures. A measure of goodness is determined for each measurement. The measure of goodness is used in generating the index.

It should be noted that the selected databases are not exclusively the reference state database and the study state database. Depending on the goals of the analysis and the sets of measurements, the states may be named in a different manner, e.g. state 1, state 2 etc. The states may correspond to the study state and to the reference state, or not.

(A) Measure of Goodness

The measure of goodness is determined for each measurement (step 62) to determine which measurements have different values in the reference state and the study state, and therefore, which measurements give reliable information on the particular state.

One possibility to determine the measure of goodness (step 63) is to use statistical tests (e.g. t-tests). One of the subgroups presented above for the study state and one of the subgroups presented above for the reference state are used in the statistical test. The result of the statistical test is a p-value that describes the probability that the differences in the measurement values between the study state and the reference state are the result of chance alone. Therefore, the smaller the p-value the more probable it is that there are real differences in the measurement values between the study state and the reference state. From the p-values of the $i^{th}$ measurement, p(i), the measure of goodness, e.g. a significance value, S(i), is computed for each measurement:

$$S(i) = \frac{\ln \min[p(i), 0.05] - \ln 0.05}{\ln 0.000001 - \ln 0.05}.$$

The significance value S(i) is zero, if the p-value is larger than 0.05 (i.e., if there are no statistically significant differences in the reference and study states), and it increases as the differences between the reference and study states become larger.

(B.1) Distance Measure

The relative distance from the reference state to the system of interest (e.g. the system data database in FIG. 6), when compared with the study state, is calculated as:

$$d(i) = \frac{m(i) - \overline{m}_R(i)}{\overline{m}_S(i) - \overline{m}_R(i)},$$

where m(i) is the $i^{th}$ measurement value of the system of interest, $\overline{m}_R(i)$ is the mean or median of the subgroup of the reference state, and $\overline{m}_S(i)$ is the mean or median of the subgroup of the study state. The d(i) value (step 64) shows how large the difference between the measurement value from the system of interest and the reference state is, and which is the direction of the difference.

The distance values of each measurement are combined using weighted averaging, in which the weightings are the measures of goodness, e.g. the computed significance values:

$$D = \frac{\sum_i S(i)d(i)}{\sum_i S(i)}.$$

The obtained value D (step 66) describes how closely the observed differences for the system data of the system of interest, when compared with the reference state, match with the corresponding differences of the study state. The larger the value is the more distinct the state of the system is. If the value is close to zero, no indications exist that the system is in the particular study state.

(B.2) Probabilistic Measure

In the probabilistic measure, it is studied how the measurement values of the system of interest fit to the distributions of the corresponding measurements of the subgroups of the reference and study states. Let us consider the case where $\overline{m}_R(i) < \overline{m}_S(i)$. The cumulative probabilities:

$P_R(i) = P(m_R(i) \geq m(i))$ and $P_S(i) = P(m_S(i) \leq m(i))$ are determined from the system data, where $m_R(i)$ and $m_S(i)$ denote the $i^{th}$ measurement values of the subgroups of the reference and study states, respectively, $\overline{m}_R(i)$ is the mean or median of the subgroup of the reference state, and $\overline{m}_S(i)$ is the mean or median of the subgroup of the study state.

In other words (step 65), it is studied how probable it is that a system in the reference state has a measurement value larger than the corresponding value of the study system, and vice versa for the study state. The cumulative probabilities can be determined with any method, for example, using the Gaussian approximation or un-parametric methods.

A fitness value for the measurement value m(i) is then obtained from:

$$f(i) = \frac{P_S(i)}{P_S(i) + P_R(i)}.$$

The f(i) value describes how well the measurement value m(i) fits to the distributions of the subgroups of the reference and study states. The larger the value is the better the measurement value fits to the distribution of the subgroup of the study state. The fitness value can obtain values between zero and 1. The value of 0.5 represents the case in which it is equally probable that the measurement value arises from a system having a state corresponding to the reference state or to the study state.

In case $\overline{m}_R(i) > \overline{m}_S(i)$, the probabilities $P_R(i) = P(m_R(i) \leq m(i))$ and $P_S(i) = P(m_S(i) \geq m(i))$ are determined. Otherwise the analysis proceeds as presented above.

If necessary, the calculated fitness values can be constrained to a specific range of values or extrapolated so that fitness values smaller than zero or fitness values larger than 1 are possible.

The fitness values of all the measurements are combined using weighted averaging, in which the weightings are the measures of goodness, e.g. the computed significance values:

$$D = \frac{\sum_i S(i)f(i)}{\sum_i S(i)}.$$

The obtained value D (step 66) describes how closely the measurement values of the system of interest match with the corresponding values in the subgroup of the study state. If the fitness values are not constrained or extrapolated, the value of D is between zero and 1. Large values are indications that the system is in the study state, and small values are indications that the system is in the reference state.

(C) Combined Analysis

Any combination of the methods presented above (the measure of goodness, the distance measure, the probabilistic measure) is possible as well.

Furthermore, the above-mentioned methods to compute the measures of goodness, the significance values, the distance values, the fitness values, and the final index are non-restrictive examples of possible methods that can be used. Any method related to the presented methods can be used as well.

For example, the subgroups (one for the reference state and one for the study state) may be used to train a regression model for the regression analysis. The independent variables of the model are the measurement values. The number of the independent variables may be reduced using a feature selection algorithm. The dependent variable of the model for the reference state is set either to a constant value or a value dependent on the statistics of the reference state. For the study group, the dependent variable is either a constant value or a value dependent on the distance values or the results of the statistical tests, as compared to the reference state. A weighted regression model may also be used, in which the weightings may be dependent on the distance values or the results of statistical tests, and/or the number of the examples in the reference and study subgroups.

When the system data is given as an input for the regression model, it gives as an output a scalar value that estimates the state of the system. The obtained values are dependent on the values of the dependent variable and used in the training of the regression model. A system in a state corresponding to the study state should obtain a value similar to the values of the dependent variable in the database of the study state, and a system in a state corresponding to the reference state should obtain a value similar to the values of the dependent variable in the database of the reference state.

(D) System Classification

In addition to studying the state of a system, the proposed method can be utilized in classifying a system. This can be carried out by comparing the data of the system with different study states (e.g. the state 1 database in FIG. 6). Then the results obtained for the different study states, i.e. the values of the measure of goodness, the distance or fitness values, and the state indices, are compared and the system is classified as the study state that is the most similar to the studied system (step 67).

(E) Visualization

From tables containing numerical data of the measurements and the statistical tests it may be difficult to perceive the most important differences between the different states or to compare the system data with the different states. On the other hand, the human visual system can effectively process information coded with colours and shapes and sizes of objects. Therefore, to make the inference easier for a human being, a visualization tool that utilizes a tree structure and arrows, pointers, indicators or colours is provided. Additionally, colour codes, sizes, shapes, location, orientation, font sizes, font styles etc., can be used to visualize the results (step 68), e.g. using boxes or squares. The figures show an example where the anatomy and function of the heart is compared with patients and healthy control subjects.

Figure 2A:
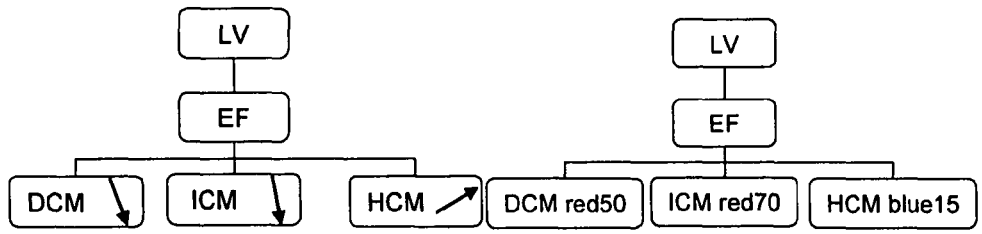
FIG. 2a illustrates a colour coded tree structure and a tree structure with pointers for an application for studying differences between diseases (DCM=dilated cardiomyopathy, ICM=ischemic cardiomyopathy, and HCM=hypertrophic cardiomyopathy).
Figure 2B:
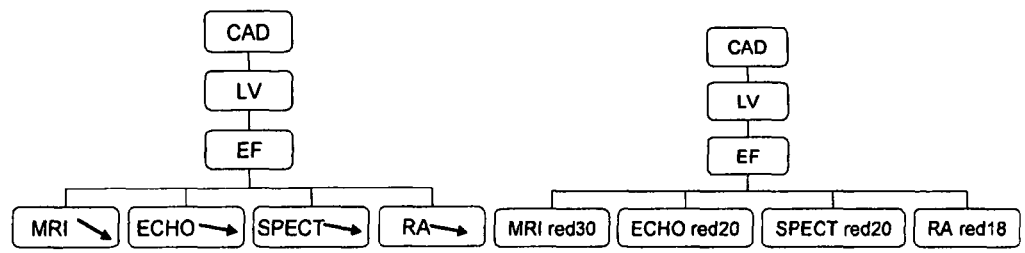
FIG. 2b illustrates a colour coded tree structure and a tree structure with pointers for an application for studying differences between imaging modalities.
Figure 2C:
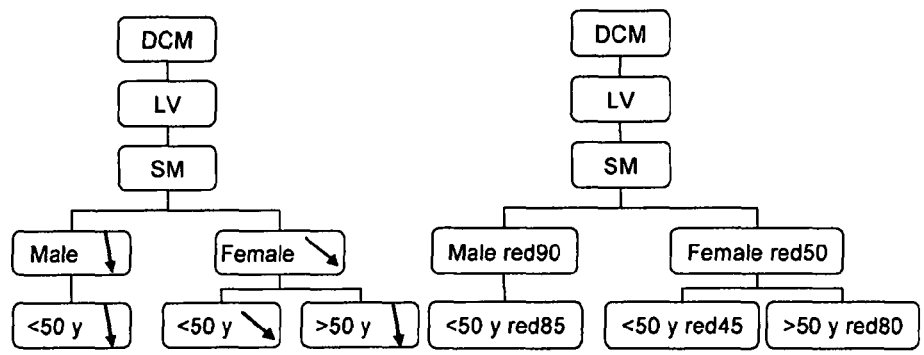
FIG. 2c illustrates a colour coded tree structure and a tree structure with pointers for an application for studying differences between populations.

The tree structure is constructed by clicking features in user-interface boxes shown in FIG. 1. The order of the selections is arbitrary. Therefore, the visualization tool can be utilized in various applications. For example, the visualization tool can be used to study the differences in several measurements between diseases, or to study the differences between age groups or genders. Three tree structures for different applications are shown in FIGS. 2*a*, 2*b* and 2*c*.

Figure 3A:
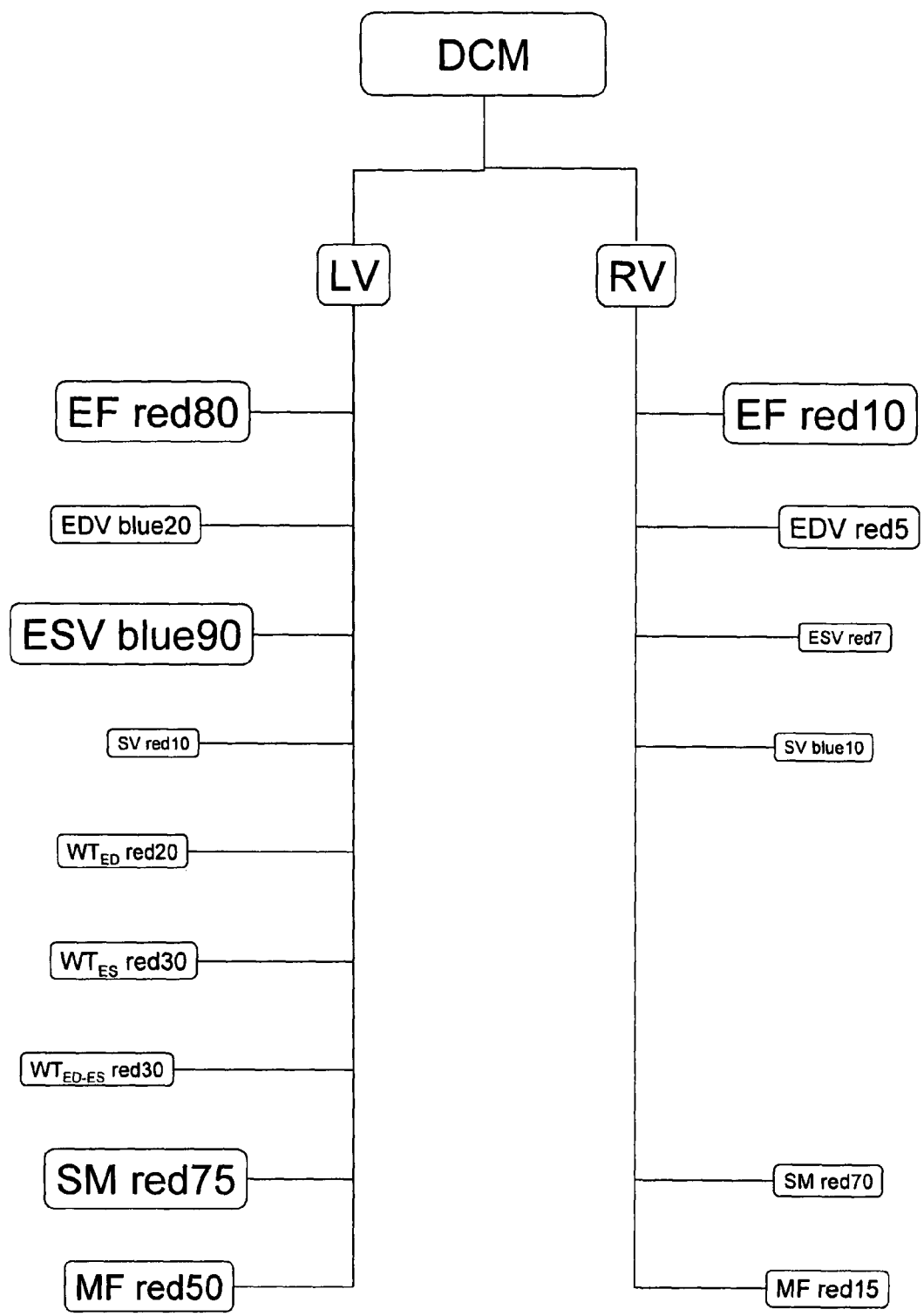
FIG. 3a illustrates the comparison of the system data with the reference state, wherein measurements for the cardiac left (LV) and right (RV) ventricles of the system are compared with the measurements of the reference state using colour codes.
Figure 3B:
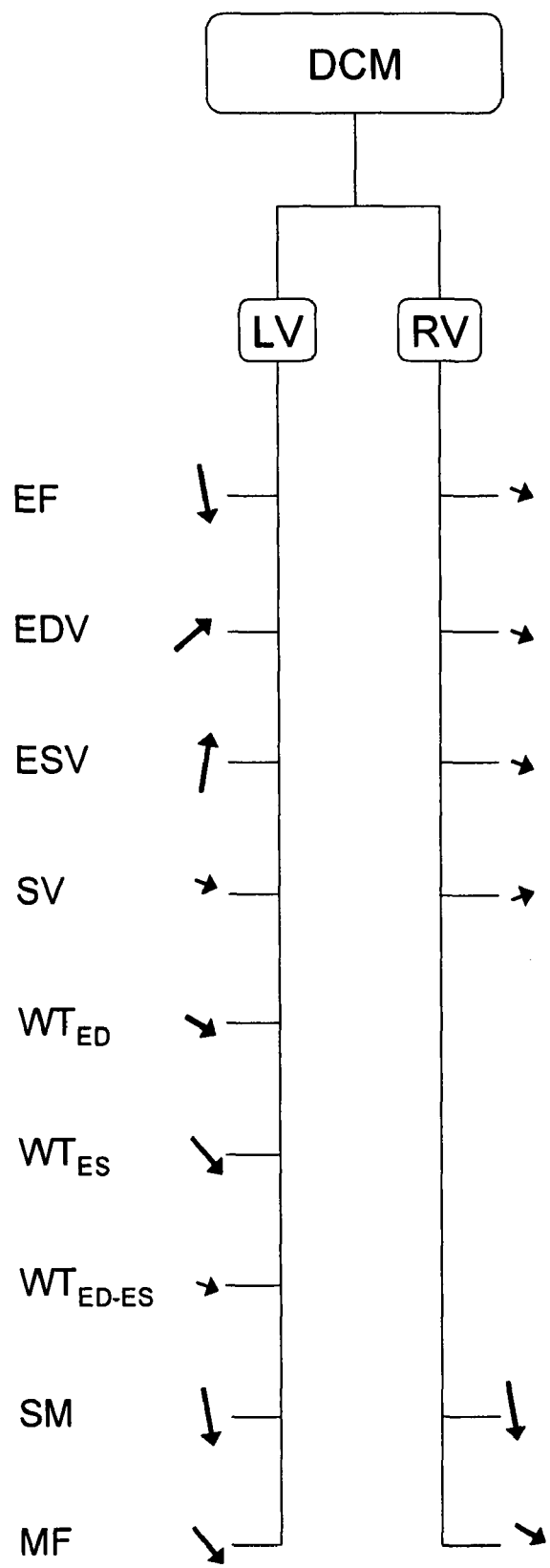
FIG. 3b illustrates the comparison of the system data with the reference state, wherein measurements for the cardiac left (LV) and right (RV) ventricles of the system are compared with the measurements of the reference state using pointers.

In FIGS. 3*a* and 3*b*, the results for the comparison of the study state (a group of patients with dilated cardiomyopathy (DCM)) with the reference state (a group of healthy subjects) are visualized. The boxes represent various measurements included in the set of measurements.

Figure 4A:
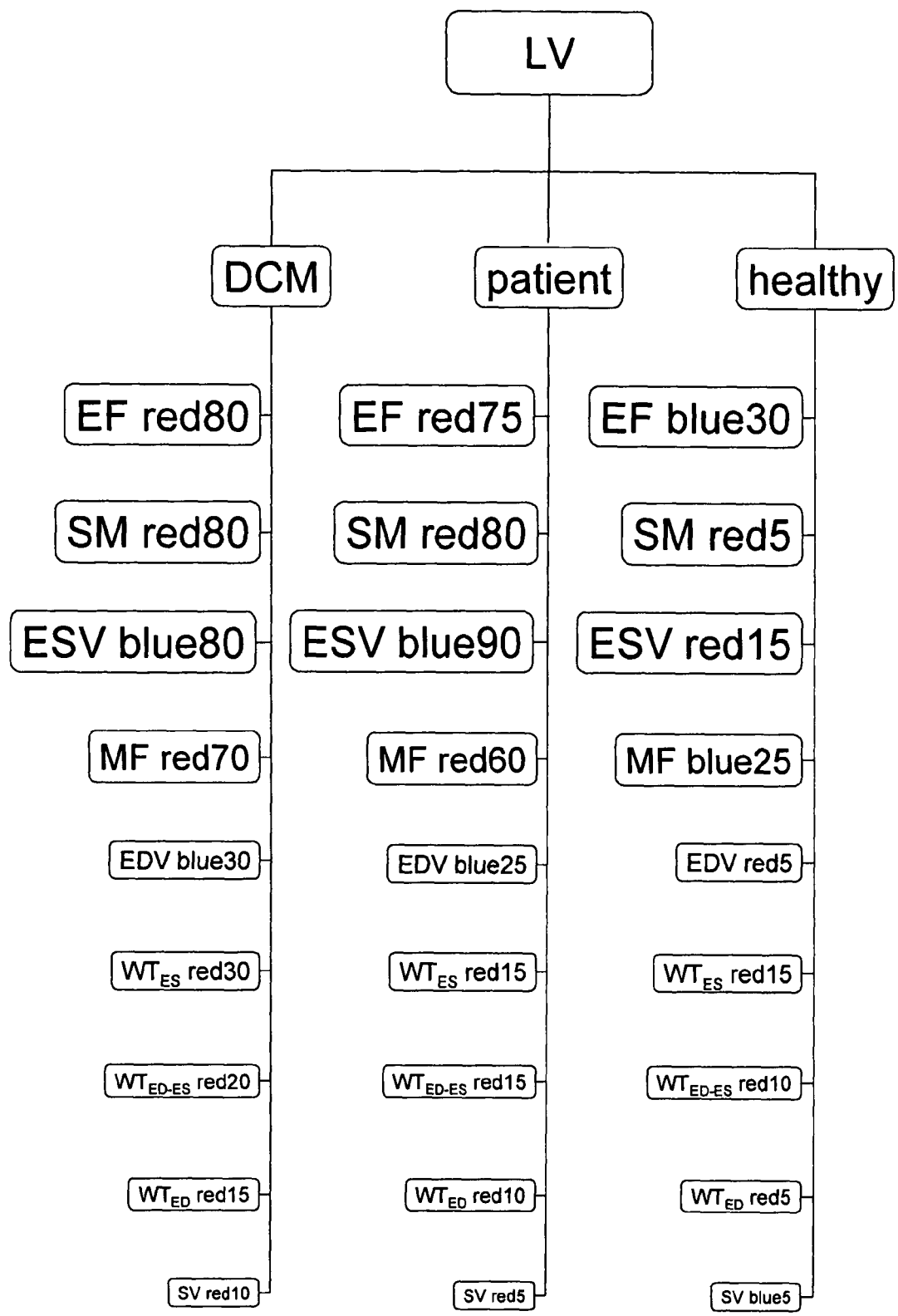
FIG. 4a illustrates the comparison of the results of typical examples of a system in the study (disease) and reference (healthy) states along with the results for a study state (DCM) using colour codes.
Figure 4B:
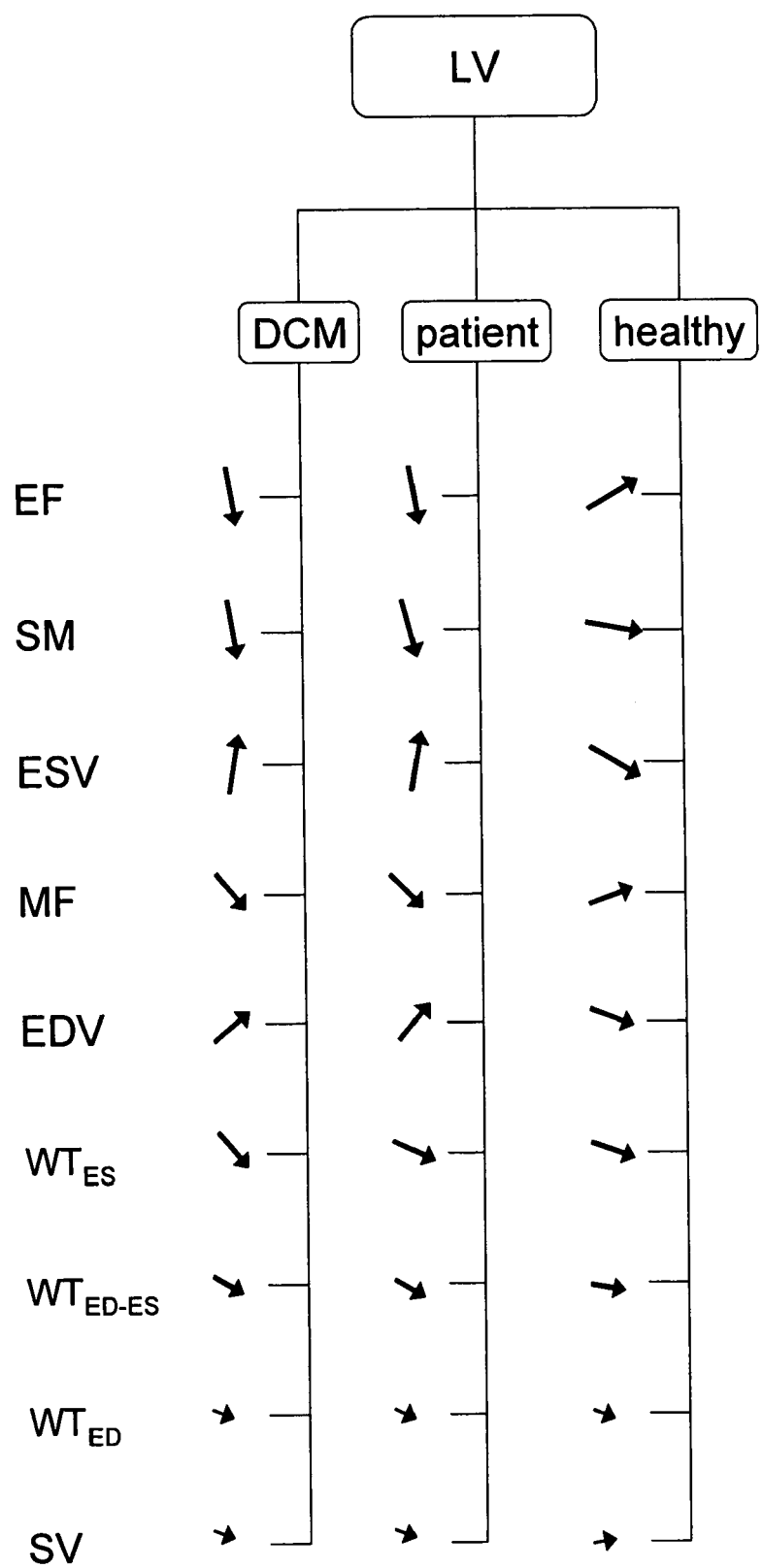
FIG. 4b illustrates the comparison of the results of typical examples of a system in the study (disease) and reference (healthy) states along with the results for a study state (DCM) using pointers.

In FIGS. 4*a* and 4*b*, typical examples of a system in the study (disease) and reference (healthy) states are compared with the reference state and the results are visualized along with the comparison for the whole study group (DCM). The boxes represent various measurements included in the set of measurements.

In FIGS. 3*b* and 4*b*, the orientations of the pointers are used to visualize the differences in the measurement values between the studied system (or the study state) and the reference state: a pointer pointing up shows that the measurement value of the system or the study state is larger than the corresponding measurement value of the reference state, and vice versa for the pointers pointing down. The size of the pointer changes in proportion to the measure of goodness determined for the measurement.

Another option is to use boxes with different colours to visualize the differences in the measurements. Blue colour is used when the measurement value of the system or the study state is larger than the corresponding measurement value of the reference state, and red colour is used when the corresponding measurement value of the reference state is larger. The darker the shade of the colour used is, the bigger the difference in relation to the reference state. FIGS. 2*a*, 2*b*, 2*c*, 3*a* and 4*a* show texts representing the colour in use and numerical values representing the saturation of the colour being included in the boxes, contrary to the actual application in which the boxes are filled in with the respective colours.

Preferably, the size of the boxes is selected to correspond to the measure of goodness, i.e. the significance value of the measurement, as shown in FIGS. 3*a* and 4*a*. The bigger the box is, the greater the significance. Preferably, in FIGS. 3*a* and 4*a*, the boxes representing the measurements are arranged according to the size of the box, and the biggest boxes are located at the top. Preferably, the measurement is represented by a shape the size of which is dependent on the significance of the measurement and the colour of the shape which is dependent on the difference of the measurement in relation to the reference state.

The differences in the measurements can be computed using e.g. the distance measure, the probabilistic measure, or the statistical tests. The pointers or boxes can be arranged, for example, based on the measure of goodness, and grouped, for example, based on what is measured.

Figure 5A:
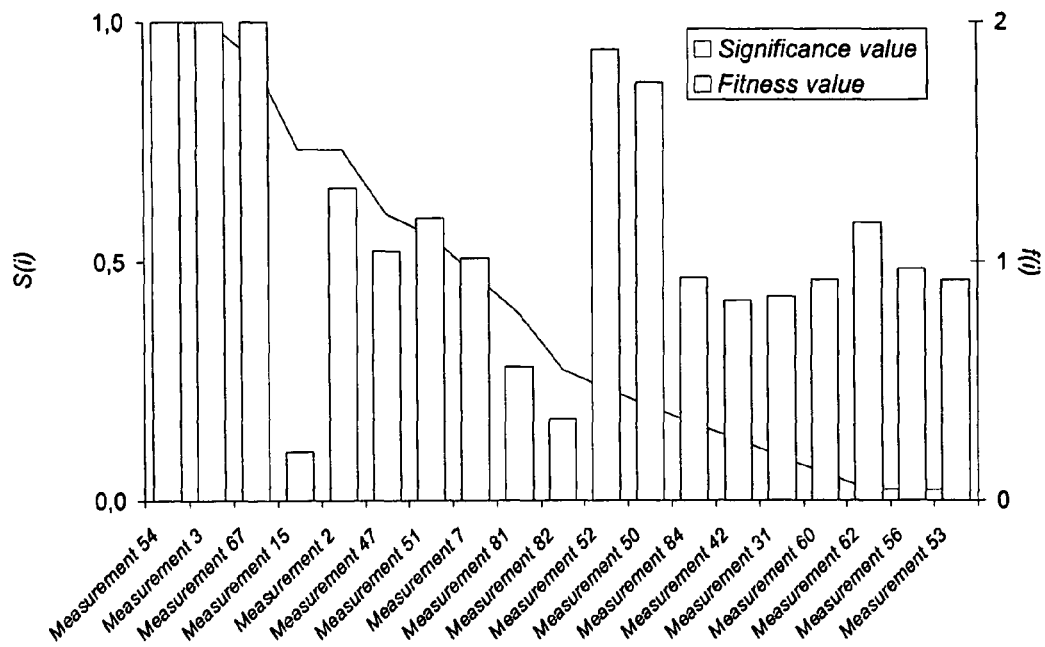
FIG. 5a illustrates fitness values in the same graph with the significance values for a system in a study state, wherein the system is a human heart, the reference state is the healthy state, and the study state is a heart disease, and wherein the measurements describe the anatomy and function of the heart.
Figure 5B:
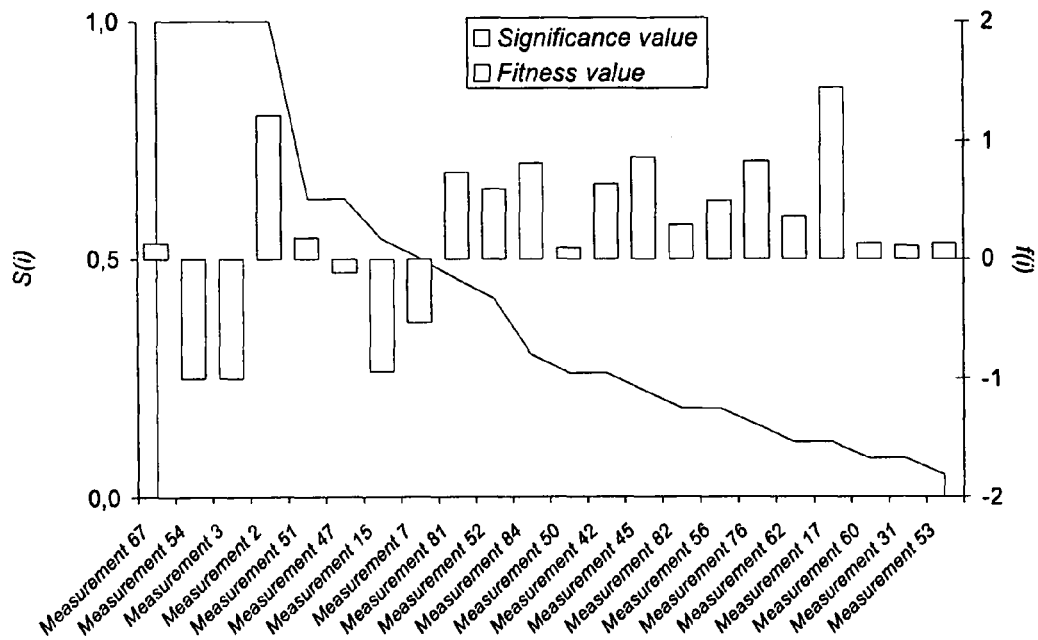
FIG. 5b illustrates fitness values in the same graph with the significance values for a system in a reference state, wherein the system is a human heart, the reference state is the healthy state, and the study state is a heart disease, and wherein the measurements describe the anatomy and function of the heart.

Alternatively or additionally, the visualization tool shows either the distance values or the fitness values in the same figure with the significance values, as shown in FIGS. 5*a* and 5*b*. The distance values or the fitness values are represented as bars extending from the value 0.0 to the calculated value of the distance value or the fitness value. The significance value is represented by a line graph in a two-dimensional, orthogonal axis system. In FIGS. 5*a* and 5*b*, the system is a human heart, the reference state is the healthy state, the study state is a heart disease, and the measurements describe the anatomy and function of the heart.

The above-mentioned methods and systems are implemented in a computer system comprising necessary input and output devices for representing the results to a user. The computer system is provided with a processor for the execution of the methods according to the invention, including the necessary program code for the execution of the application running in the computer system. Preferably, the computer system comprises a graphical user interface, GUI, for the implementation of the invention. The computer system comprises necessary memory and storages devices for storing the system data related to the measurements and the study and reference states.

Figure 7:
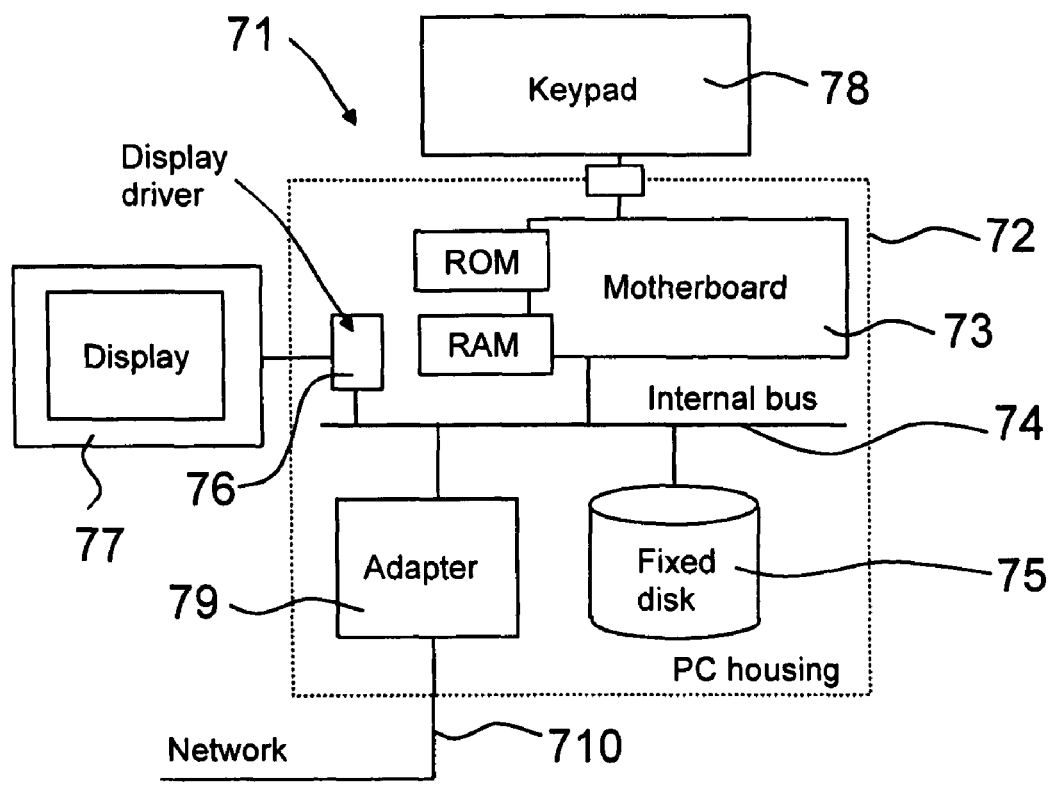
FIG. 7 illustrates the assembly of a typical computer device in which the invention may be carried out.

FIG. 7 shows, on a principle level, the assembly of a typical computer device 71, which is a personal computer (PC) device. The device 71 is normally placed in a housing 72, and it comprises a mother board 73 with a central processing unit (CPU), the necessary ROM memories (BiosROM), as well as an internal bus 74 to which it is possible to connect various components, such as a network adapter 79 which is further connected to a network 710. The necessary memory components for a working memory (RAM) are also connected to the mother board 73. Further, the device 71 comprises a keypad 78, through which the data are entered, and a display, on which information is displayed. A fixed disk 75 is used for storage, also including an operating system to control the operation of the device 71, application software being run under its control, and the necessary device drivers to control the operation of the different components, for example a display driver 76 for the display 77. In the selection and operation of the components, it is possible to apply techniques and methods known as such, as well as to select the necessary peripheral devices. Typically, the device is also provided with a diskette drive or a CD drive for reading various means in which software products are stored for distribution and installation on the fixed disk 75. The fixed disk 75 is used for the storage of data in different forms, for example in a database. The software comprising the necessary program code and complying with the methods presented above is run in the device 71 according to a embodiment of the invention.

Inasmuch as the present invention is subject to many variations, modifications and changes in detail, it is intended that all matters described throughout this specification and shown in the accompanying drawings be interpreted as illustrative only and not in a limiting sense. Accordingly, it is intended that the invention be limited only by the scope of the hereto appended claims.

The invention claimed is:

1. A computer implemented method, comprising:
computing a measure of goodness for each of at least two dimensions of a system linked to a first state of the system and a second state of the system;
computing a difference measure for each of at least two dimensions linked to a studied system, the difference measures describing the differences of said at least two dimensions in relation to said first state and said second state; and
displaying at least one of said measures of goodness and said difference measures in a graphical presentation for inferring the state of the studied system.

2. The method of claim 1, further comprising:
computing a state index based on said measures of goodness and said difference measures; and
inferring the state of the studied system based on said measures of goodness and said difference measures.

3. The method of claim 1, further comprising:
selecting said first state as a reference state with which the state of the studied system and said second state are compared.

4. The method of claim 1, further comprising:
computing a further measure of goodness for each of at least two dimensions of the system linked to a third state of a system;
computing a further difference measure for each of at least two dimensions linked to said studied system, the difference measures describing the difference of said at least two dimensions in relation to said first state and said third state;
inferring the state of the studied system based on said further measures of goodness and said further difference measures; and
classifying the studied system based on said measures of goodness, said further measures of goodness, and said difference measures.

5. The method of claim 1, further comprising:
selecting a first subgroup comprising at least one example, each example representing the system linked to said first state, or selecting a second subgroup comprising at least one example, each example representing the system linked to said second state, or selecting both said first subgroup and said second subgroup.

6. The method of claim 1, further comprising:
computing each difference measure using a distance measure based on a relative distance value, or using a probabilistic measure based on a fitness value; or
computing each measure of goodness using a significance value based on statistical tests.

7. The method of claim 1, wherein the state of the system relates to a disease and the system relates to a human body.

8. The method of claim 1, further comprising:
determining said at least two dimensions from medical imaging data.

9. The method of claim 1, further comprising:
displaying said measures of goodness and said difference measures in a tree structure.

10. The method of claim 9, further comprising:
displaying at least one of said measures of goodness in a graphical presentation for inferring the state of the studied system; or displaying both at least one of said measures of goodness and at least one of said difference measures in a graphical presentation; the graphical presentation comprising at least one corresponding measure of goodness for said first state, or said second state, or both; or the graphical presentation comprising both at least one corresponding measure of goodness and at least one corresponding difference measure for said first state, or said second state, or both.

11. The method of claim 9, wherein the graphical presentation is provided with shapes or symbols representing at least one of said at least two dimensions, said measure of goodness being indicated by an arrow, an indicator, or a pointer, or by the shade of the colour in the shape or the symbol, or the size of the shape or the symbol, and said difference measure being indicated by the direction of the arrow, the indicator, or the pointer, or by the shade of the colour in the shape or the symbol; and wherein the graphical presentation is preferably a list, a matrix, or a tree structure.

12. An apparatus, programmed to:
compute a measure of goodness for each of at least two dimensions of a system linked to a first state of the system and a second state of the system;
compute a difference measure for each of at least two dimensions linked to a studied system, the difference measures describing the differences of said at least two dimensions in relation to said first state and said second state; and
display at least one of said measures of goodness and at least one of said difference measures in a graphical presentation for inferring the state of the studied system.

13. The apparatus of claim 12, the apparatus being further programmed to:
compute a state index for inferring the state of the studied system, the state index being based on said measures of goodness and said difference measures.

14. The apparatus of claim 12, the apparatus being further programmed to:
display both said measures of goodness and said difference measures in a graphical presentation for inferring the state of the studied system.

15. The apparatus of claim 12, the apparatus being further programmed to:
display at least one of said measures of goodness in a graphical presentation for inferring the state of the studied system; or displaying both at least one of said measures of goodness and at least one of said difference measures in a graphical presentation; the graphical presentation comprising at least one corresponding measure of goodness for said first state, or said second state, or both; or the graphical presentation comprising both at least one corresponding measure of goodness and at least one corresponding difference measure for said first state, or said second state, or both.

16. The apparatus of claim 12, the apparatus further comprising:
a processor for computing said measures of goodness and said difference measures;
a display for displaying at least one of said measures of goodness or said difference measures, or both; and
a database system for storing at least one example representing the system linked to said first state, at least one example representing the system linked to said second state, and at least one example representing the studied system.

17. A computer program product comprising program code stored on a computer-readable medium, said program code comprising:
an instruction to compute a measure of goodness for each of at least two dimensions of a system linked to a first state of the system and a second state of the system;
an instruction to compute a difference measure for each of at least two dimensions linked to a studied system, the difference measures describing the differences of said at least two dimensions in relation to said first state and said second state; and an instruction to display at least one of said measures of goodness and at least one of said difference measures in a graphical presentation for inferring the state of the studied system.

18. The computer program product of claim 17, said program code further comprising:

an instruction to compute a state index for inferring the state of the studied system, the state index being based on said measures of goodness and said difference measures.

19. The computer program product of claim 17, said program code further comprising:

an instruction to display both said measures of goodness and said difference measures in a graphical presentation for inferring the state of the studied system.

20. The computer program product of claim 17, said program code further comprising:

an instruction to display at least one of said measures of goodness in a graphical presentation for inferring the state of the studied system; or displaying both at least one of said measures of goodness and at least one of said difference measures in a graphical presentation; the graphical presentation comprising at least one corresponding measure of goodness for said first state, or said second state, or both; or the graphical presentation comprising both at least one corresponding measure of goodness and at least one corresponding difference measure for said first state, or said second state, or both.

21. The apparatus according to claim 12, wherein the apparatus is further programmed to:

display said measures of goodness and said difference measures in a graphical tree structure.

22. The computer program product according to claim 17, wherein said program code further comprises:

an instruction to display said measures of goodness and said difference measures in a graphical tree structure.

* * * * *

UNITED STATES PATENT AND TRADEMARK OFFICE
CERTIFICATE OF CORRECTION

PATENT NO. : 7,840,510 B2  Page 1 of 1
APPLICATION NO. : 11/798583
DATED : November 23, 2010
INVENTOR(S) : Juha Koikkalainen et al.

It is certified that error appears in the above-identified patent and that said Letters Patent is hereby corrected as shown below:

Title Page item 30

Please include the priority history on the face of the patent, as follows:

--Finland Application No. 20065327, Filed May 15, 2006--.

Signed and Sealed this
Nineteenth Day of April, 2011

David J. Kappos
*Director of the United States Patent and Trademark Office*